United States Patent
Van Dyck et al.

(10) Patent No.: US 7,001,625 B2
(45) Date of Patent: *Feb. 21, 2006

(54) SOLID PHASE SYNTHESIS OF SALTS OF ORGANIC ACIDS INCLUDING BUTYRIC ACID

(75) Inventors: Stefaan Van Dyck, Brasschaat (BE); Clifford Adams, Antwerp (BE); Andre Meeuwsen, Schilde (BE); Leen van Campenhout, Geel (BE)

(73) Assignee: Kemin Industires, Inc., Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/342,598

(22) Filed: Jan. 15, 2003

(65) Prior Publication Data

US 2004/0010040 A1    Jan. 15, 2004

Related U.S. Application Data

(63) Continuation-in-part of application No. 09/918,383, filed on Jul. 30, 2001.

(51) Int. Cl.
C07C 55/00 (2006.01)
C07C 51/42 (2006.01)
C07C 59/08 (2006.01)
A23K 1/00 (2006.01)
A23L 1/216 (2006.01)

(52) U.S. Cl. .......... 426/54; 426/96; 562/580; 562/589; 562/590; 562/595; 562/607; 562/609

(58) Field of Classification Search .......... 71/11; 426/74, 96, 428, 606, 54; 562/599, 606, 562/589, 580, 590, 595, 607, 609; 549/315
See application file for complete search history.

(56) References Cited

U.S. PATENT DOCUMENTS

| 3,519,571 A | 7/1970 | Szczepanek |
| 3,880,968 A | 4/1975 | Kasper |
| 3,944,606 A | 3/1976 | Rieger |

(Continued)

FOREIGN PATENT DOCUMENTS

CN    1060580    4/1992

(Continued)

OTHER PUBLICATIONS

Williams, Barbara; Verstegen, M.W.A.; Tamminga, V.; Tamminga, S.; "Fermentation in the Large intestine of Single-Stomached Animals and its Relationship to Animal Health"; pp. 207-227; Feb. 2001; Nutrition Research Reviews.

(Continued)

*Primary Examiner*—Cecilia J. Tsang
*Assistant Examiner*—Taylor Victor Oh
(74) *Attorney, Agent, or Firm*—Kent A. Herink; Daniel A. Rosenberg; Emily E. Harris (57) ABSTRACT

A process for the solid-phase synthesis of salts of organic acids in a granular, free-flowing, and dust-free form particularly suited for use as animal feed additives. A mixture of liquid organic acids, including butyric acid, is applied to an inert, absorbent carrier. A solid base is then added during stirring. The acid is slowly released from the carrier preventing the fast reactions that lead to the formation of clumps. The exothermic reaction releases heat which assists in reducing the moisture content of the product. The addition of butyric acid results in a product which has an improved effect on animal growth over the animal feed additive without the addition of butyric acid.

13 Claims, 3 Drawing Sheets

U.S. PATENT DOCUMENTS

| | | | |
|---|---|---|---|
| 4,337,722 | A | 7/1982 | Debayeux |
| 4,353,709 | A | 10/1982 | Nioh |
| 4,700,000 | A | 10/1987 | Merkel et al. |
| 4,735,967 | A | 4/1988 | Neesby |
| 4,853,233 | A | 8/1989 | McAskie |
| 4,946,654 | A | 8/1990 | Uhlemann |
| 4,988,520 | A | 1/1991 | Overton |
| 4,996,067 | A | 2/1991 | Kobayashi et al. |
| 4,997,469 | A | 3/1991 | Moore |
| 5,019,148 | A | 5/1991 | Moore |
| 5,045,459 | A | 9/1991 | Mothes |
| 5,149,643 | A | 9/1992 | Mothes |
| 5,221,673 | A | 6/1993 | Zoltan |
| 5,250,714 | A | 10/1993 | Lajoie |
| 5,453,365 | A | 9/1995 | Stetzel |
| 5,549,890 | A | 8/1996 | Kubo |
| 5,766,439 | A | 6/1998 | Eyal |
| 5,795,615 | A | 8/1998 | Nelson |
| 5,935,625 | A | 8/1999 | Hjørnevik et al. |
| 5,935,635 | A | 8/1999 | Mori et al. |
| 6,068,862 | A | 5/2000 | Ishihara et al. |
| 6,137,005 | A | 10/2000 | Hjørnevik |
| 6,153,246 | A | 11/2000 | Gossart |
| 6,210,681 | B1 | 4/2001 | Walker |
| 6,238,709 | B1 | 5/2001 | Kalmbach |

FOREIGN PATENT DOCUMENTS

| | | |
|---|---|---|
| CN | 1124137 | 6/1996 |
| CN | 1249301 | 4/2000 |
| CN | 1267661 | 9/2000 |
| EP | 1000552 A1 | 5/2000 |
| EP | 1155623 | 11/2001 |
| ES | 8608290 | 12/1986 |
| FR | 2785807 A1 | 11/1998 |
| GB | 2103616 | 2/1983 |
| RU | 2136173 | 9/1999 |
| WO | WO 0003723 | 1/2000 |

OTHER PUBLICATIONS

Paulicks, B.R.; Roth, F.X.; Kirchgessner, M.; "Dose Effects of Formi on the Performance of Growing Piglets"; Agrobiol. Res. 49; pp 318-326 (1996).

Overland, M., Granli, T., Kjos, N.P., Fjetland, O., Steien, S.H., Stokstad, M.; "Effect of Dietary Formates on Growth Performance, Carcass Traits, Sensory Quality, Intestinal Microflora, and Stomach alterations in growing-finishing pigs"; J. Animal Sci. 78; pp 1875-1884 (2000).

Sociedad Anonima Alniser; "Adimix Butyrate"; Leaflet; Spain Feb. 9, 1999.

Sociedad Anonima Alniser; "MSDS Adimix"; Spain; Feb. 9, 1999.

Galfi, P., Gabel, G., Marten, H.; "Influences of extracellular matrix components on the growth and differentiation of ruminal epithelial cells in primary culture"; Research in Veterinary Science 54; pp 102-109 (1993).

Baldwin, R.L., Jesse, B.W.; "Propionate Modulation of Ruminal Ketogenesis"; J. Animal Science 74; pp 1694-1700; 1996.

Galfi, P., Bokori, J.; "Feeding Trial in Pigs with a Diet Containing Sodium n-Butyrate"; Acta Veterinaria Hungarica 38; pp 3-17; 1990.

Galfi, P., Neogrady, S.; "Alimentation Animale et Sante Publique Additifs Sans Residus Probiotiques-Preprobiotiques"; France; May 17, 1995.

Galfi, P., Neogrady, S.; "acides organiques monocarboxyliques (2-6 carbones) dans la nutrition des porcs et autres especes"; France. 1992.

Van Der Wielen, P.W.J.J., Beesterveld S., Notermans, S., Hofstra, H., Urlings, A.A.P., Van Knapen, F. "Role of volatile fatty acids in development of the cecal microflora in broiler chickens during growth"; Applied and Environmental Micrcobiology; 66; pp 2536-2540; 2000.

Vernay, M., Marty, J.; "Absorption and metabolism of butyric acid in rabbit hind gut"; Com. Biochem, Physiol; 77A; pp 89-96.(1984).

Finnie, I.A., Dwarakanath, A.D., Taylor, B.A., Rhodes, J.M.; "Colonic mucin synthesis is increased by sodium butyrate"; Gut 36; pp 93-99; (1995).

Meeusen, I.A.; "Improving egg shell quality in older laying hens"; Kemin Europa; pp 1-6; Apr. 2002.

Van Campenhout, L., Vermeesen, N., Mertens, K.; "The development of buffered acid lac Part II: in vitro performance compared to acid lac dry"; Kemin Companies; pp 1-8; Dec. 2002.

Peys, E., Coppens, B., Van Dyck, S., Meeusen, A.; "The effect of buffered acid lac dry with or without calcium butyrate on broiler performance as an alternative to antibiotic growth promoters"; Kemin Companies; pp 1-5; Apr. 2002.

Van Dyck; S., Coppens, B.; "The development of buffered acid lac Part I: solid phase synthesis of salts of organic acids"; Kemin Companies; pp 1-9; Jan. 2002.

Belyavin, C.; "An investigation undertaken on behalf of Kemin Europa NV looking at a number of starter diet formulations in the feed of broiler chickens between 1 and 15 days of age"; Trial report for Kemin Europa NV; Mar. 2001.

European Commission; "Second opinion on anti-microbial resistance"; http://europa.eu.int/comm/food/fs/sc/ssc/out203_en.pdf; May 2001.

Xeris, S.A.; competition product PA 625; http://www.xeris-online.com/English/pa625.htm; May 2001.

Chemaly Z., et al. Crystallization Kinetics of calcium lactate in a mixed-suspension-mixed-product removal crystallizer. Industrial & Engineering Chemistry Research. 38: (7) 2803-2808 Jul., 1999.

Van Halsema, et al. The modeling of carbon dioxide-aided extraction of carboxylic acids from aqueous solutions. Industrial & Engineering Chemistry Research. 37: (3) 748-758 Mar., 1998.

Miller, RW, et al. Extraction of lactic acid from a calcium lactate solution using amine-containing solvents and carbon dioxide gas. Industrial & Engineering Chemistry Research. 35: (4) 1156-1162 Apr., 1996.

SOLID PHASE SYNTHESIS OF SALTS OF ORGANIC ACIDS INCLUDING BUTYRIC ACID

This application is a continuation-in-part application of Ser. No. 09/918,383, filed Jul. 30, 2001.

BACKGROUND OF THE INVENTION

The invention relates generally to the synthesis of salts of organic acids and, more specifically, to the solid phase synthesis of salts of organic acids, including butyric acid, in a dust-free form and particularly suited for use as animal feed additives.

Salts of organic acids are widely used in the animal feed industry as preservatives of the animal feed and as sources of acids in animal feed rations. The salts disassociate in the digestive tract of the animal and provide a number of advantageous effects, including the maintenance of a healthy gastric environment and a beneficial microbial balance. Monogastric animals, such as swine and poultry, must keep a low gastric pH to maintain a healthy gut. Low gastric pH is one of the major factors governing the performance of monogastric animals and the economics of livestock production. The pH of the gut may rise when the animals are young or under stress. The addition of salts of organic acids to the animal feed ration helps to maintain a low gastric pH and to improve the health of the animal.

Salts of butyric acid will have an acidifying effect, but because of its distinct alkyl chain, it will have a different activity and selectivity when compared to salts of other fatty acids, such as formic, acetic, and propionic acid. Salts of butyric acid also have an important function on the intestinal morphology of the gut. The addition of butyrates leads to an increased surface area of the gut wall due to an increase in size of the villi. The increased surface area aids the absorption of nutrients and promotes animal growth.

A satisfactory animal feed acidifier product must function as an acidifier, blend with the animal feed ration, be acceptable to the animal, and not grossly alter the physical characteristics of the animal feed. Problems have occurred in the production of animal feed acidifiers in the form of clumping of the acidifier during manufacture, requiring an additional processing step to comminute the acidifier to a size where it can be blended with the animal feed ration, be acceptable to the animal, and provide a bioavailable source of the organic acid upon ingestion. Comminution of clumps can result in the production of fines, i.e., finely divided particles that create dustiness, resulting in a loss of product during mixing into the animal feed ration and an unpleasant environment for persons conducting the mixing. Other methods of producing these products have required an additional energy-consuming step to remove excess water, such as distillation or spray drying. There is needed a method of producing salts of organic acids that results in a feed acidifier that has a small particle size without the presence of fines, which does not clump during formation and which does not require additional drying.

Animal feed acidifiers are commonly added to animal rations that also include mineral premixes. Many of the mineral premixes include either or both amino acids and copper sulfate. These ingredients react with the volatile acids of the animal feed acidifier to form clumps. There is a need for a method of producing salts of organic acids that does not cause clumping when combined with mineral premixes including either amino acids or copper sulfate. In addition, the lack of volatile acids in the animal feed acidifier of the present invention means it will not react with the butyrates.

SUMMARY OF THE INVENTION

The invention consists of a method of synthesizing salts of organic acids, including butyric acid, using solid phase synthesis. A mixture of butyric acid and at least one other liquid organic acid is added to an acceptable, inert carrier. A solid base is added during mixing. The acid is slowly released from the carrier preventing the fast reactions that lead to the formation of clumps. The exothermic reaction releases heat which assists in reducing the moisture content of the product. The process can be repeated to increase the loading of the salt on the carrier. The resulting product is comprised of free-flowing granules. The average particle size increases slightly with the number of repetitions of adding the acid and base to the carrier. A loading of between about 65% and 80% of the organic acid salt on the carrier can be easily achieved, depending in part on the characteristics of the organic acid being used, without undue clumping of the product.

When even small amounts of salts of butyric acid and an alkali metal are present, a synergistic effect is obtained over formulations not including the butyrate.

An object of the invention is to provide a method of synthesizing salts of an organic acid in form that is free-flowing and of a small particle size relatively free of dust, particularly suited for use as an animal feed acidifier.

Another object of the invention is to provide a method of synthesizing salts of an organic acid that is adaptable to adjust the loading of the organic salt on an inert carrier.

Still another object of the invention is to provide an animal feed acidifier including butyrates which has an improved effect on growth of the animal over a feed acidifier not including butyrates.

These and other objects of the invention will be made apparent to those skilled in the art upon a review of this specification and the appended claims.

DETAILED DESCRIPTION OF PREFERRED EMBODIMENTS

The method generally comprises the addition of a liquid organic acid to an inert carrier in an amount sufficient to moisten the carrier. Of particular importance is the addition of at least a small amount of butyric acid. A dry base is slowly added to the moistened carrier during mixing. The base reacts with the acid as it is relatively slowly released from the carrier. The slow release of the acid prevents the fast reaction that can lead to clumping. Additionally, the heat released during the exothermic reaction between the acid and base assists in reducing the moisture content of the mixture. If desired, once the moisture content of the mixture has been reduced, additional liquid acid can be added to the mixture, followed by the adding of additional base, in order to increase the loading of the organic salt on the carrier.

Organic acids suitable for use in the present process are all liquid organic acids. Preferred organic acids include lactic acid, propionic acid, acetic acid, and formic acid and mixtures thereof. In addition, butyric acid is included as an organic acid used in the formulation. Bases suitable for use in the present process include alkali metal hydroxides and alkaline-earth metal bases, including calcium oxide, calcium hydroxide, sodium hydroxide and potassium hydroxide and mixtures thereof. Carbonates, such as calcium carbonate, sodium carbonate, and sodium bicarbonate, cannot be used as the sole bases in the reaction because of the formation of carbon dioxide during the reaction with the acids and because the reaction is not sufficiently exothermic to complete drying of the product. These bases may be used, however, in combination with the preferred bases.

During the first loading of the carrier with the liquid acid, it is preferable to avoid excess wetting of the carrier. A preferred range of the weight ratio of carrier to acid is between about 1:1 and 3:1, and more preferably, between about 1.5:1 and 2:1, giving consideration to the water content of the acid being used. For example, using lactic acid (80% feed grade), a ratio of 2:1 can be used, whereas when using propionic acid, a ratio of 1.5:1 is the preferred maximum.

The total loading of the carrier can be increased by repeated cycles of adding acid and base to the carrier. The maximum preferred loading that can be obtained is dependent on the acid. For lactic acid (80% feed grade), a preferred product is obtained until the product contains about 65% calcium lactate and 35% carrier. Further loading of the salt on the carrier makes the product more difficult to process as it becomes sticky. Also, the size profile of the granules of the product changes as the loading is increased above a certain level. Above about 65%, granules in the range of 0.5 to 1 cm appear, with a fraction even larger. For propionic acid, a preferred product is obtained until the product contains about 80% calcium propionate and 20% carrier. Further loading, while presenting no processing difficulties, begins to result in increased dustiness. This may be because the newly produced salt is no longer in contact with the carrier. Dustiness can be reduced, even at a loading above 80%, by the addition of a small amount of feed grade lactic acid.

Additional free acids in their solid form, such as fumaric or ascorbic acid, can be incorporated into the product after the last salt formation reaction. The free acids are preferably added when the temperature of the mixture is observed to start to drop. The acids are thus incorporated into the granules of the product during the drying process. In the same way, other powdered or granular materials can be incorporated into the product, such as mineral salts, minerals, antioxidants, or amino acids. A loading of up to about 50% of such additional ingredients can usually be obtained with the ingredient being incorporated into the product granules. Additional loading of the added ingredients can be made, but not all of the added ingredient may be incorporated into the granules.

In this process water and heat are produced. The reaction heat evaporates water to assist in obtaining a dry product. Care should be taken to respect the time that is needed to evaporate the water. The reaction time is controlled by the speed at which the organic acid mixture and the dry mixture are added. When the reagents are added to quickly the mixture doesn't have enough time to evaporate all the water that is being formed. Adding acids and bases step-wise is used to control the evaporation. After each addition, the blend is mixed for a short period of time until it has dried sufficiently. It is also possible to add acids and bases in a continuous process. In that case the rate of the addition is preferably lower in order to allow "in-process" drying. In that case the production of water and the evaporation are preferably adjusted to be in equilibrium.

EXPERIMENT 1

Solid Phase Synthesis of a Mixture of Salts

Small Batch: Twenty-one grams of lactic acid (food grade=80%) and 9 g propionic acid were combined and divided into three equal fractions. Calcium hydroxide, 10.256 g, and 0.862 g of calcium oxide are combined, mixed, and divided into three equal fractions. The first fraction of the acid combination is added to 20 g of almond shell meal while stirring. Then, the first fraction of the combined base mixture is slowly added while stirring. The temperature of the mixture is observed to increase and water starts evaporating. When the product appeared to be dry, the same procedure was repeated for the remaining fractions, adding the acid while stirring, adding the base while stirring and drying.

This method produced a non-dusty granulated product.

In an alternative experiment, a small amount (approx. 1 $cm^3$) of butyric acid was added to the acid mixture before dividing. A similar product resulted.

Large Batch: One hundred and thirty kilograms of lactic acid (food grade=80%), 110 kg propionic acid, and 8.9 kg of butyric acid were combined. Calcium hydroxide, 60 kg, and 38.4 kg of calcium oxide were combined and mixed. One hundred and sixty kilograms of almond shell meal and 103 kg of dry fumaric acid were added to the mixer (horizontal ribbon blender; 1000 liter; central outlet size of 200 mm; operated at 20 rpm). While stirring, the liquid acid mixture was added to the mixer at a rate of approximately 3.55 kg/min and the dry base mixture was added at a rate of approximately 3.59 kg/min. The total time for adding the liquid acid and dry base mixtures is typically about 70 minutes. After 70 minutes, the mixer is operated for an additional time of approximately 15 minutes to complete drying of the product. Of course, the addition rates and drying times will depend on the type and size of mixer employed. It is also possible to start with less almond shell meal and no fumaric acid and add the additional almond shell meal and fumaric acid after the liquid acid mixture and dry base have all been added. Of course, various other ingredients to be included in the final feed additive product can also be added after the addition of the liquid acids and dry base while the final stirring and drying stage is being completed in the mixer.

This method produced a non-dusty granulated product.

EXPERIMENT 2

Synergistic Effect of the Combination of Organic Acids and Sodium Butyrate on the Growth Prameters of Boilers.

In a broiler trial four different treatments were used in order to evaluate the possible synergistic effect between organic acids and sodium butyrate.

This pen trial included eight replicates of four treatments (Table 1). Each pen had 74 mixed sex commercial Ross broiler chicks. Birds were fed a wheat-based diet including enzymes. All birds were weighed on days 1, 5, 10 and 15. The composition of the acid mixture is given in Table 2. The performance parameters at day 15 are given in Table 3. The results show the synergistic effect between organic acids and sodium butyrate. The feed conversion ratio based on weight gain of the treatment using only sodium butyrate or only a mixture of acids is not statistically different from the control group. On the other hand the combination of organic acids and sodium butyrate is significantly different from the other treatments (P<0.039).

TABLE 1

Treatments for Early Chick Growth

| Group | Ingredient | |
| --- | --- | --- |
| | Acid mixture | Na-butyrate(g/tonne) |
| A | None | None |
| B | None | 80 |
| C | 5000 | None |
| D | 3000 | 40 |

TABLE 2

Composition of the acid mixture used in the broiler trial

| Ingredient | Amount % |
| --- | --- |
| Fumaric acid | 45 |
| Lactic acid | 20 |
| Formic acid | 1 |
| Propionic acid | 1 |
| Citric acid | 1 |
| Carrier (water, silica) | 32 |

TABLE 3

Chick performances to 15 days

| Performance parameter | Treatment[1] | | | |
| --- | --- | --- | --- | --- |
| | A | B | C | D |
| Feed consumed (g/bird) | 437.4 | 441.3 | 451.1 | 459.9 |
| Weight gain (g/bird) | 349.1a | 358.4a | 367.4a | 382.4b |
| FCR based on wt gain | 1.278a | 1.279a | 1.259a | 1.239b |

[1]Treatment means within the same row not sharing a same letter differ statistically significant (P<0.05)

These trials show clearly that a combination of organic acids and sodium butyrate triggers a specific biochemical mechanism "in vivo" that leads to a synergistic effect of the combination of the ingredients. If there would be no new biochemical processes or interactions involved only an additive effect would be observed.

An important advantage of the synergism is the possibility to use lower concentrations of the acid mixture and the butyrate and still retain a significant improvement of the growth parameters, compared with the individual ingredients.

EXPERIMENT 3

Synergistic Effect of the Combination of Organic Acids, Calcium Salts of Organic Acids and Calcium Butyrate.

The objective of this trial was to study and compare two formulations (Table 4) with organic acids and calcium salts of organic acids. One of the formulations included calcium butyrate. Both formulations were compared with a positive and negative control in order to evaluate their possible growth promoting effect evaluated by broiler performance.

Twelve-hundred Ross broilers were divided over 40 floor pens. Each pen contained 15 male and 15 female Ross broilers, one tube feeder and one bell drinker. Feed and water were available ad libitum. All birds received a broiler starter feed from day 0 until day 11 and a broiler finisher meal from day 11 until day 39. The basic feeds did not contain any growth promoter or coccidiostat. Pens were assigned to one of four treatments (ten replicate pens for each treatment) using a block randomization. The in feed treatments consisted of: A. no treatment (negative control); B. Avilamycine 10 g/ton (positive control, dosed as Maxus G200 at 50 g/ton); C. Mixture 1, 5000 g/ton and D. mixture 2, 5000 g/ton. In the broiler house the temperature program started on day 0 at 31° C. decreasing 1° C. every two days until 21° C. was reached. The day-night cycle was 23 hours light and 1 hour dark. All birds were weighed at days 0, 11, 25, and 39. Feed usage was measured at days 11, 25 and 39. Live performance data were analyzed as a randomized block design with pen means as the statistical unit. Statistical analysis was performed with Figurepad Instat 2.0 and Microsoft Excel Analysis Toolpak software.

TABLE 4

Composition (%) of formulation 1 (without calcium butyrate) and formulation 2 (with calcium butyrate)

| Ingredient | Formulation 1 | Formulation 2 |
| --- | --- | --- |
| Inert carrier | 25.4 | 25.4 |
| Calcium lactate | 26 | 26.0 |
| Calcium propionate | 28.6 | 26.8 |
| Calcium butyrate | 0 | 2.0 |
| Fumaric Acid | 16.6 | 16.6 |
| Rapeseed oil | 2.3 | 2.1 |
| Sugars/water | 1.1 | 1.1 |

The effect of different treatments on chick performance is shown in Table 5. On day 25 the positive control group receiving Avilamycine performed better than the negative control group concerning weight gain. This difference in weight gain was statistically significant (P<0.05). Only a treatment with formulation 2 resulted in a performance comparable with that of the positive control group. Formulation 1 did not perform any better than the negative control group. On day 39 the group receiving formulation 2 matched the positive control group concerning both weight gain and feed conversion ratio. Both these groups performed better than the negative control group. Weight gain differences were statistically significant. All treatments resulted in a feed conversion ratio (FCR) that was numerically better than that of the negative control group on day 39. The treatment with formulation 2 was the only one that resulted in an improved FCR with statistical significance (P<0.05). It also appears that the presence of the calcium butyrate leads to an extra gain of weight when the groups receiving formulation 1 and 2 are compared.

These results show that the combination of salts of organic acids and free organic acids leads to significant synergistic effects on the growth parameters when used in combination with calcium butyrate. Formulation 2 also had the same effect on the growth parameters as the antibiotic growth promoter.

TABLE 5

Average feed conversion ratio (FCR) and average weight gain (WG) of different treatment groups with their standard deviation; treatment means within the same row not sharing a same letter differ statistically significant (P < 0.05)

|  |  | Negative control | Avilamycine 10 g/ton | Formulation 1 | Formulation 2 |
|---|---|---|---|---|---|
| WG(g) | Day 11 | 222 ± 13 a | 227 ± 7 a | 218 ± 9 a | 221 ± 11 a |
|  | Day 25 | 811 ± 40 a | 853 ± 44 b | 808 ± 30 a | 830 ± 21 ab |
|  | Day 39 | 1868 ± 62 a | 1981 ± 58 b | 1895 ± 70 a | 1978 ± 57 b |
| FCR | day 11 | 1.316 ± 0.047 a | 1.314 ± 0.034 a | 1.333 ± 0.022 a | 1.331 ± 0.043 a |
|  | day 25 | 1.813 ± 0.085 a | 1.775 ± 0.135 a | 1.758 ± 0.066 a | 1.737 ± 0.043 a |
|  | day 39 | 1.877 ± 0.030 a | 1.839 ± 0.061 ab | 1.834 ± 0.038 ab | 1.822 ± 0.042 b |

EXPERIMENT 4

Synergistic Effect of Non-volatile Organic Acids and Calcium Salts of Organic Acids in Combination with Calcium Butyrate on the Performance Parameters of Laying Hens.

six hundred one ear old laying hens of the breed Isa-Brown were divided in three groups and housed in cages of 5 hens per cage. Groups of eight cages were contiguous and formed a group of 40 hens that were allocated to a treatment.

The treatments were as follows: (a) Control group: receiving a commercial feed, without animal proteins and without AGP; (b) formulation 1 group: received 3 kg of formulation 1 on top of the commercial formula; (c) formulation 2 group: received 3 kg of formulation 2 on top of the commercial formula.

The trial design covered 3 treatments×5 repetitions×40 hens during a trial period of two times 4 weeks. All parameters were measured at the end of each 4-week period.

Tables 6 and 7 show the average performances of the laying hens over the 8 weeks period and Table 8 gives the average parameters on egg shell quality, measured on ⅓rd of the eggs.

TABLE 6

Effects on laying performances: average of 2 periods of 4 weeks

| Lay parameter | Control | Formulation 1 | Formulation 2 |
|---|---|---|---|
| Laying percentage, % | 84.5 | 86.1 | 87.1 |
| Mortality, % | 0.7 | 1.2 | 0.5 |
| Egg mass, g/hen/day | 57.4 | 57.2 | 57.9 |

TABLE 7

Effects on feed intake and FCR: average of 2 periods of 4 weeks

| | Treatment | | |
|---|---|---|---|
| Growth Parameter | Control | Formulation 1 | Formulation 2 |
| Daily feed intake, g/hen | 130.7 | 130.3 | 128.2 |
| FCR | 2.278 | 2.278 | 2.217 |

TABLE 8

Effects on egg quality: average of 2 periods of 4 weeks

| | Treatment | | |
|---|---|---|---|
| Eggshell quality parameter | Control | Formulation 1 | Formulation 2 |
| Broken eggs, % | 0.62 | 0.60 | 0.61 |
| Specific gravity index | 1.087 | 1.088 | 1.087 |
| Shell thickness, mm | 0.299 | 0.322 | 0.314 |

Figure 1:
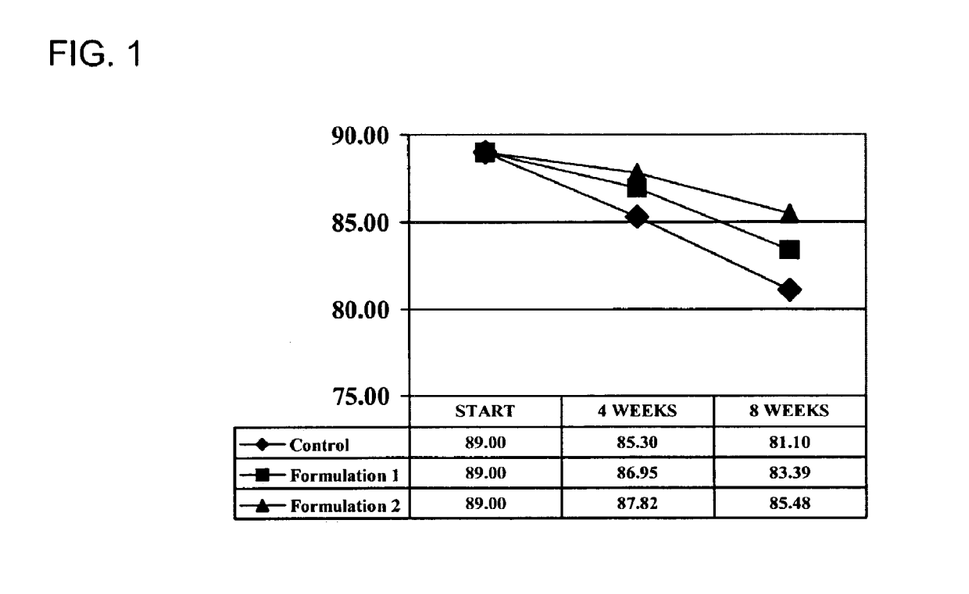
FIG. 1 is a graphical representation of the laying percentage.
Figure 2:
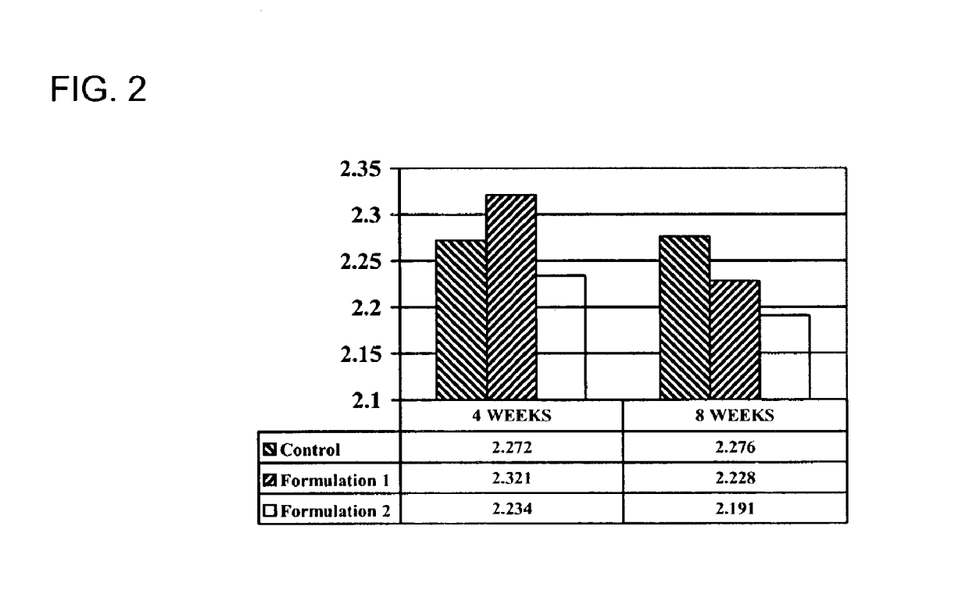
FIG. 2 is a graphical representation of the feed conversion ratio.
Figure 3:
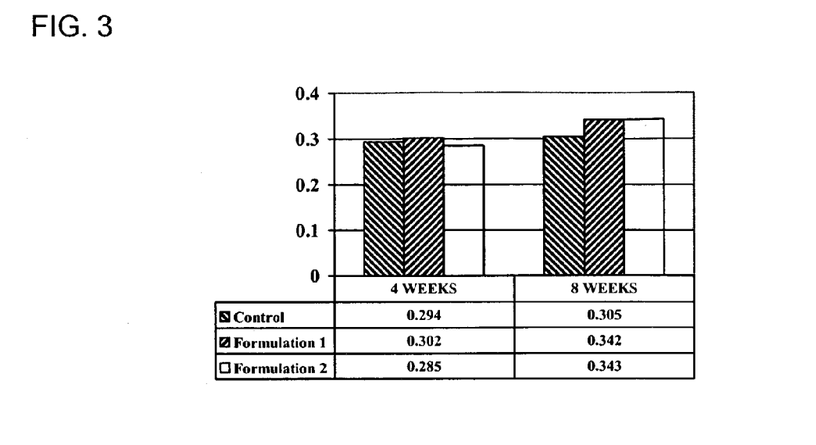
FIG. 3 is a graphical representation of eggshell thickness.

Considering a normal decrease in laying percentage at that age of around 0.55% per week, the egg production is above standards. The use of formulation 2 improves the layer performance and feed conversion ratio numerically better than formulation 1. For the eggshell quality formulation 2 is equivalent to formulation 1. This phenomenon might be explained by the fact that the quality of the eggshell is mostly influenced by the calcium content of the formulations. Because of the limited difference in calcium content between formulation 1 and 2, no significant differences should be expected for the eggshell quality parameters. The evolution of the lay, growth and eggshell parameters in function of time is also clearly in favor of formulation 2, which includes the calcium butyrate. The differences of al the performance parameters between the treated groups and the control group become more important after a longer period of addition of the formulation to the feed. This is clearly demonstrated in FIGS. 1–3. Considering a normal decrease in laying percentage at standards and seems to be in favor of formulation 2.

EXPERIMENT 5

The Effect of Non-volatile Organic Acids and Calcium Salts of Organic Acids and their Combination with Calcium Butyrate on the in Vitro Eubiotic Effect Using a Cultured Inoculum.

An improvement of the condition of the gastro-intestinal tract in general may well be obtained by regulating thebalance of the microbial flora (eubiosis) and has a beneficial effect on the health and growth of animals. The influence of formulation 1 and 2 on a mixture of two representative microorganisms was investigated in an in vitro assay (minimum inhibition concentration). The Gram-positive *Lactobacillus fermentum* was used as a reference organism for the beneficial lactic acid flora. A strain of the Gram-negative *Salmonella enteritidis* was used as a possibly harmful organism. In the assay the gastrointestinal conditions were simulated by mean of mixing an amount of ground feed raw material with buffer, a microbial cell suspension and the product. The tests were performed using a buffer of pH 4.25 to simulate the gastric conditions. A second buffer at pH 6.5 was used to simulate conditions further in the digestive tract. Both microorganisms were added together in the medium to test the influence of each other's presence on the response of their individual growth to the test products. Also in the animals' digestive tract both organisms are present.

It is very obvious that requirements for new antimicrobials/acidifiers are (1) that they do not inhibit beneficial organisms, as represented here by *Lactobacillus fermentum* and (2) that they inhibit or kill harmful organisms represented here by *Salmonella enteritidis*. The results of the in vitro tests are presented in FIGS. 4 and 5.

Figure 4:
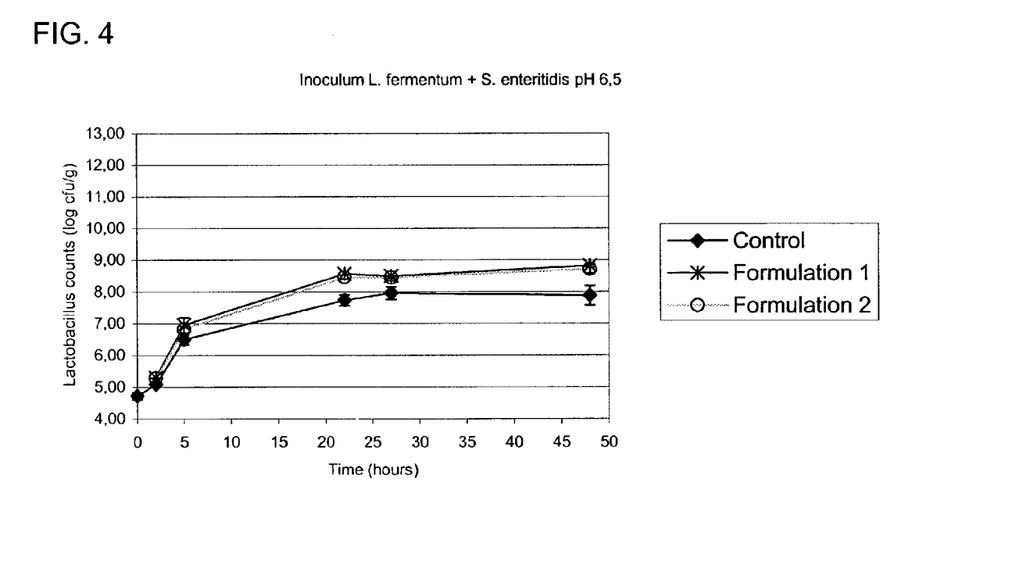
FIGS. 4 and 5 are graphical representations of the bacteriostatic effect of the feed additive of the present invention.
Figure 5:
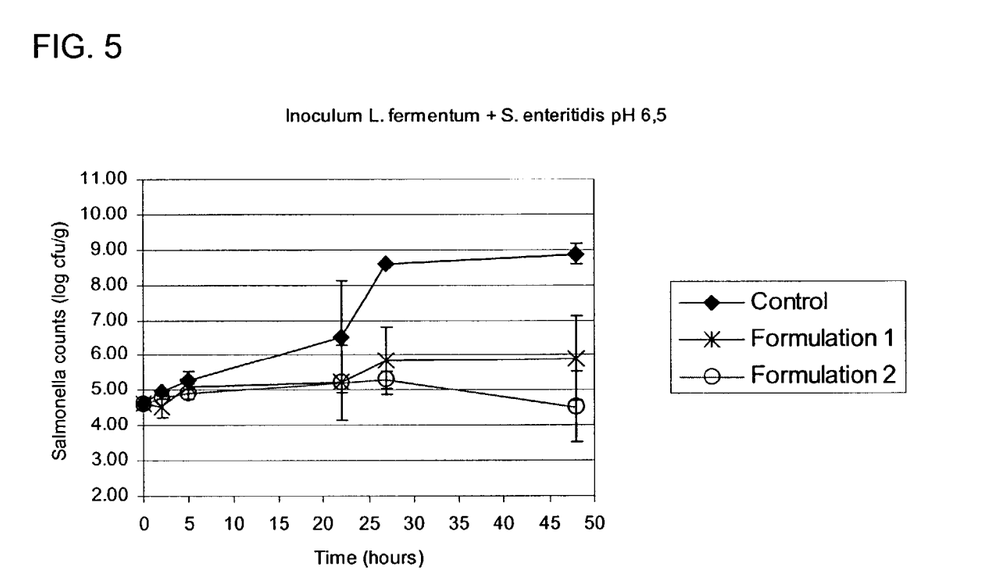

In summary, neither formulation inhibited *L. fermentum* in the presence of *S. enteritidis*. On the other hand, the *S. enteritidis* counts decreased after the addition of the formulations. Because there are no consistent differences between both formulations, the butyrate did not negatively influence the formulation, and that the existence of an eubiotic effect of a mixture of organic acids and calcium salts of organic acids in combination with calcium butyrate was confirmed by MIC tests.

EXPERIMENT 6

The Effect of Non-volatile Organic Acids and Calcium Salts of Organic Acids and their Combination with Calcium Butyrate on the In Vitro Eubiotic Effect Using a Natural Inoculum In this experiment 10 g of barley was added a flask together with buffer and an inoculum prepared from a faeces sample in a 10–1 dilution. An acid mixture (Table 2) and formulation 2 were added to the mixture in order to evaluate the eubiotic effect. The literature proves that freshly passed faeces collected under strictly anaerobic conditions could be considered as representative of the large-intestinal flora (Williams, B. A., Verstegen, M. W. A., and Tamminga, S.(2001) Fermentation in the large intestine of single-stomached animals and its relationship to animal health, *Nutrition Research Reviews*, 14, 207–227).

The Lactobacilli growth was determined after 0, 26 and 50 hours of incubation at 37° C. in a waterbath.

TABLE 9

Lactobacilli counts (cfu/g)

| Time (h) | Control | Acid mixture | Formulation 2 |
|---|---|---|---|
| 0 | $2.44 \cdot 10^6$ | | |
| 26 | $7.90 \cdot 10^{10}$ | $3.24 \cdot 10^{10}$ | $1.89 \cdot 10^{10}$ |
| 50 | $5.76 \cdot 10^7$ | $9.34 \cdot 10^7$ | $1.07 \cdot 10^9$ |

The positive effect from formulation 2 compared with an acid mixture can be clearly observed from these data, and proves the eubiotic effect.

EXPERIMENT 7

The Effect of Non-volatile Organic Acids and Calcium Salts of Organic Acids and their Combination with Calcium Butyrate on the in Vivo Eubiotic Effect.

At the end of a performance trial with 156 piglets (Piétrain×Hybride), 4 treatments×2 genders×2 replicates×9–11 piglets per pen), a sample of faeces was taken for every group. The obtained samples were subjected to microbial counts. The order of magnitude of enterobacteriaceae and lactic acid bacteria counts are presented in Table 10.

TABLE 10

Microbial counts of faeces (in cfu/g)

| | Treatment | | | |
|---|---|---|---|---|
| Microorganism | Control (antibiotics) | Acid mixture | Formulation 1 | Formulation 2 |
| Total enterobacteriaceae | $10^3$ | $10^4$ | $10^3$ | $<10^3$ |
| Lactic acid bacteria | $3.38 \cdot 10^7$ | $1.5 \cdot 10^6$ | $2.06 \cdot 10^7$ | $2.20 \cdot 10^7$ |

The composition of the acid mixture is given in Table 2.
The composition of formulation 1 and 2 is given in Table 3.

These data demonstrate that formulation 2 brings about the best eubiotic effect of the series. One can also conclude that an acid mixture is less effective than a mixture of non-volatile organic acids and calcium salts of organic acids. The presence of a small amount of calcium butyrate in formulation 2 improves the eubiotic even further.

EXPERIMENT 8

Inclusion of Additional Compounds

The method also may be practiced wherein other ingredients or compounds are incorporated into the granulate. Examples of such ingredients are solid organic acids (e.g., citric acid, ascorbic acid, and fumaric acid), mineral salt solutions (e.g., copper sulfate), natural or synthetic surfactants, flavorings, colorants, and pigments. In a specific example, to 30 g of almond shell meal, 15 g or a diluted solution of one of the foregoing additional ingredients is added while stirring. Thereafter, 10 g or the organic acid is added, followed by and equivalent amount of the selected base, all while stirring. When the temperature of the mixture drops below 35° C. the procedure is repeated twice more.

The foregoing description comprise illustrative embodiments of the present inventions. The foregoing embodiments and the methods described herein may vary based on the ability, experience, and preference of those skilled in the art. Merely listing the steps of the method in a certain order does not necessarily constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A process for the preparation of a granular organic acid salt animal feed supplement, comprising the steps of:
   (a) combining in a reaction vessel an inert carrier and a mixture of butyric acid and at least one other liquid organic acid which is absorbed by the carrier;
   (b) adding to the reaction vessel an inorganic base which reacts with the organic acids in an exothermic reaction to produce a granular organic acid salt animal feed supplement; and
   (c) allowing the organic acid salt animal feed supplement to dry without the use of additional sources of heat.

2. A process as defined in claim 1, further comprising the step of repeating the steps of adding one or more organic acids in the mixture of organic acids and adding the base.

3. A process as defined in claim 1, wherein the carrier is selected from the group consisting of a plant material, silica gel, and combinations of the plant material and silica gel.

4. A process as defined in claim 1, wherein the other organic acid is selected from the group consisting of acetic, ascorbic, citric, formic, fumaric, lactic, and propionic acids.

5. A process as defined in claim 1, wherein the base is selected from the group consisting of alkali metal hydroxides.

6. A process as defined in claim 1, wherein the base is selected from the group consisting of alkaline-earth metal bases.

7. A process as defined in claim 6, wherein the alkaline-earth metal bases are selected from the group consisting of oxides of alkaline-earth metals.

8. A process as defined in claim 7, wherein the oxides of alkaline-earth metals are selected from the group consisting of calcium hydroxide and calcium oxide.

9. A process as defined in claim 1, wherein the weight ratio of carrier to organic acid is in the range of between about 1:1 and about 3:1.

10. A process as defined in claim 1, wherein the amount of base used is sufficient to react with the amount of acid.

11. A process as defined in claim 2, wherein the steps are repeated until the weight ratio of organic salt to carrier is in the range of between about 1.5:1 and about 4:1.

12. A process for the preparation of a granular organic acid salt animal feed supplement, comprising the steps of:
   (a) combining in a reaction vessel an inert carrier a mixture of butyric acid and at least one other liquid organic acid which is absorbed by the carrier;
   (b) and then adding to the reaction vessel an organic base, selected from the group consisting of alkali metal bases and alkaline-earth metal bases, which reacts with the organic acids in an exothermic reaction to produce a granular organic acid salt animal feed supplement; and
   (c) allowing the organic acid salt animal feed supplement to dry without the use of additional sources of heat.

13. A method as defined in claim 12, wherein the weight ratio of carrier to organic acid is in the range of between about 1:1 and about 3:1.

* * * * *

UNITED STATES PATENT AND TRADEMARK OFFICE
CERTIFICATE OF CORRECTION

PATENT NO. : 7,001,625 B2
DATED : February 21, 2006
INVENTOR(S) : Van Dyck et al.

It is certified that error appears in the above-identified patent and that said Letters Patent is hereby corrected as shown below:

<u>Title page,</u>
Item [73], Assignee, should read -- Kemin Industries, Inc. --.

Signed and Sealed this

Second Day of May, 2006

JON W. DUDAS
*Director of the United States Patent and Trademark Office*

UNITED STATES PATENT AND TRADEMARK OFFICE
CERTIFICATE OF CORRECTION

PATENT NO. : 7,001,625 B2  
APPLICATION NO. : 10/342598  
DATED : February 21, 2006  
INVENTOR(S) : Van Dyck et al.

Page 1 of 1

It is certified that error appears in the above-identified patent and that said Letters Patent is hereby corrected as shown below:

On Title Page, Item (75) Col. 1 should read,  
Inventors: André Meeusen, Schilde (BE)

Signed and Sealed this

Eighth Day of August, 2006

JON W. DUDAS  
*Director of the United States Patent and Trademark Office*